(12) United States Patent
Schuetz et al.

(10) Patent No.: US 10,463,863 B2
(45) Date of Patent: Nov. 5, 2019

(54) HIGH CURRENT FLEXIBLE FEEDTHROUGH FOR USE WITH A POWER CONVERTER

(71) Applicant: General Electric Company, Schenectady, NY (US)

(72) Inventors: Tobias Schuetz, Bavaria (DE); Robert Roesner, Bavaria (DE)

(73) Assignee: General Electric Company, Schenectady, NY (US)

( * ) Notice: Subject to any disclaimer, the term of this patent is extended or adjusted under 35 U.S.C. 154(b) by 201 days.

(21) Appl. No.: 15/662,808

(22) Filed: Jul. 28, 2017

(65) Prior Publication Data

US 2018/0117342 A1    May 3, 2018

Related U.S. Application Data

(60) Provisional application No. 62/414,404, filed on Oct. 28, 2016.

(51) Int. Cl.

| | |
|---|---|
| *G01V 3/00* | (2006.01) |
| *A61N 1/375* | (2006.01) |
| *H01B 7/08* | (2006.01) |
| *H01B 17/28* | (2006.01) |
| *H01B 17/38* | (2006.01) |
| *H01B 17/50* | (2006.01) |
| *H02G 3/22* | (2006.01) |
| *H01G 4/35* | (2006.01) |
| *H05K 1/02* | (2006.01) |

(52) U.S. Cl.
CPC ............. *A61N 1/3754* (2013.01); *H01B 7/08* (2013.01); *H01B 17/28* (2013.01); *H01B 17/38* (2013.01); *H01B 17/50* (2013.01); *H01G 4/35* (2013.01); *H02G 3/22* (2013.01); *H05K 1/0231* (2013.01); *H05K 2201/0311* (2013.01); *H05K 2201/058* (2013.01); *H05K 2201/10272* (2013.01)

(58) Field of Classification Search
CPC .. A61B 5/055; G01R 33/4828; G01R 33/543; G01R 33/5608
USPC ......................................................... 324/318
See application file for complete search history.

(56) References Cited

U.S. PATENT DOCUMENTS

| | | |
|---|---|---|
| 4,109,298 A | 8/1978 | Hanni et al. |
| 4,747,019 A | 5/1988 | Ito et al. |

(Continued)

FOREIGN PATENT DOCUMENTS

| | | |
|---|---|---|
| EP | 2 608 406 A1 | 6/2013 |
| KR | 101318780 B1 | 10/2013 |
| KR | 101331944 B1 | 11/2013 |

OTHER PUBLICATIONS

Oka et al., "Effect of a shielding plane connected to ground plane of a PCB in EMI reduction", Electromagnetic Compatibility, 1999 International Symposium on, pp. 204-207, May 17-21, 1999, Tokyo.

(Continued)

*Primary Examiner* — Walter L Lindsay, Jr.
(74) *Attorney, Agent, or Firm* — Armstrong Teasdale LLP

(57) ABSTRACT

A feedthrough includes a first printed circuit board, a first flexible conductive element coupled to and extending from an edge of the first printed circuit board, a second printed circuit board, and a second flexible conductive element coupled to and extending from an edge of the second printed circuit board.

29 Claims, 7 Drawing Sheets

(56) References Cited

U.S. PATENT DOCUMENTS

| | | | | |
|---|---|---|---|---|
| 4,912,597 A | * | 3/1990 | Carpenter | H01G 4/38 |
| | | | | 361/329 |
| 5,157,325 A | * | 10/1992 | Murphy | G01R 1/07335 |
| | | | | 324/72.5 |
| 5,165,055 A | | 11/1992 | Metsler | |
| 5,901,040 A | | 5/1999 | Cromwell et al. | |
| 6,305,975 B1 | | 10/2001 | Steiner | |
| 6,515,870 B1 | | 2/2003 | Skinner et al. | |
| 7,525,825 B2 | | 4/2009 | Korich et al. | |
| 8,411,460 B2 | | 4/2013 | Ou et al. | |
| 9,433,090 B2 | | 8/2016 | Atkinson et al. | |
| 2003/0139096 A1 | | 7/2003 | Stevenson et al. | |
| 2011/0212639 A1 | * | 9/2011 | Paquette | H01R 12/721 |
| | | | | 439/260 |
| 2013/0234519 A1 | * | 9/2013 | Maeda | H02J 7/34 |
| | | | | 307/64 |
| 2015/0070848 A1 | * | 3/2015 | Zemke | H05K 7/2039 |
| | | | | 361/720 |

OTHER PUBLICATIONS

Alshargabi et al., "High speed PCB & spiral with patch EBG planar integration for EMI reduction", Computer, Communications, and Control Technology (I4CT), 2015 International Conference on, pp. 584-588, Apr. 21-23, 2015, Kuching.

International Search Report and Written Opinion issued in connection with corresponding PCT Application No. PCT/US2017/056659 dated Feb. 6, 2018.

\* cited by examiner

HIGH CURRENT FLEXIBLE FEEDTHROUGH FOR USE WITH A POWER CONVERTER

CROSS REFERENCE TO RELATED APPLICATIONS

This application claims the benefit of U.S. Provisional Patent Application No. 62/414,404, filed Oct. 28, 2016, which is hereby incorporated by reference in its entirety.

BACKGROUND

The field of the disclosure relates generally to feedthroughs, and more particularly, to a high current flexible feedthrough for use with a high switching frequency and high switching speed power electronics system.

At least some feedthroughs are used in large-scale power electronics systems to conduct electrical current from a power source or load, through an enclosure, to a system within the enclosure. In particular, some feedthroughs are used to conduct direct current or low frequency alternating current from a power source or load, through a cabinet, to a power converter housed within the cabinet. Within the cabinet, the power converter converts the direct electrical current to alternating electrical current for use as electrical power.

Many known power converters include fast switching semiconductor switching elements, such as silicon transistors and silicon carbide ("SiC") and gallium nitride switching elements. Such fast switching semiconductor switching elements are capable of reducing switching losses through increased switching speed, and so afford an advantage over more conventional power converters. However, the increased switching transitions and larger switching frequency of fast switching power converters may result in the production of undesirable high frequency electromagnetic energy, which may flow back over a power line, and other structures connecting the power converter via the feedthrough to remaining system, causing the power line and/or other structures, to act as unwanted antenna transmitters. The feedthroughs provide a low impedance path to ground to short circuit the unwanted high frequency energy to ground and prevent radiation of other structures within an associated power electronics system.

BRIEF DESCRIPTION

In one aspect, a feedthrough is provided. The feedthrough includes a first printed circuit board, a first flexible conductive element coupled to and extending from an edge of the first printed circuit board, a second printed circuit board, and a second flexible conductive element coupled to and extending from an edge of the second printed circuit board.

In another aspect, an electrical power conversion system is provided. The electrical power conversion system includes a cabinet comprising an outer perimeter and an inner perimeter, in which the inner perimeter defines a passage. The electrical power conversion system further includes an electrically conductive element that has a first surface and a second surface axially opposed to the first surface, and that extends through the passage. The electrical power conversion system further includes a first printed circuit board, a first flexible conductive element coupled to and extending from an edge of the first printed circuit board, a second printed circuit board, and a second flexible conductive element coupled to and extending from an edge of the second printed circuit board.

In yet another aspect, an electrical power generation system is provided. The electrical power generation system includes a power source, a cabinet comprising an outer perimeter and an inner perimeter, in which the inner perimeter defines a passage, and a power converter mounted within the cabinet. The electrical power generation system further includes an electrically conductive element having a first end and a second end, and a first surface and a second surface axially opposed to the first surface. The electrically conductive element extends through the passage and is coupled to the power source at the first end and to the power converter at the second end. The electrical power generation system further includes a first printed circuit board, a first flexible conductive element coupled to and extending from an edge of the first printed circuit board, a second printed circuit board, and a second flexible conductive element coupled to and extending from an edge of the second printed circuit board.

In yet another aspect, a feedthrough is provided. The feedthrough includes a printed circuit board, and a flexible conductive element coupled to and extending from an edge of the printed circuit board.

In yet another aspect, an electrical power generation system is provided. The electrical power generation system includes a cabinet, a power converter enclosed within the cabinet, and a feedthrough. The feedthrough includes at least one electrical assembly, at least one flexible conductive element coupled to an extending from an edge of the at least one electrical assembly, and an electrically conductive element extending between the cabinet and the power converter, the electrically conductive element in electrical contact with the at least one flexible conductive element

DRAWINGS

These and other features, aspects, and advantages of the present disclosure will become better understood when the following detailed description is read with reference to the accompanying drawings in which like characters represent like parts throughout the drawings, wherein.

Figure 1:
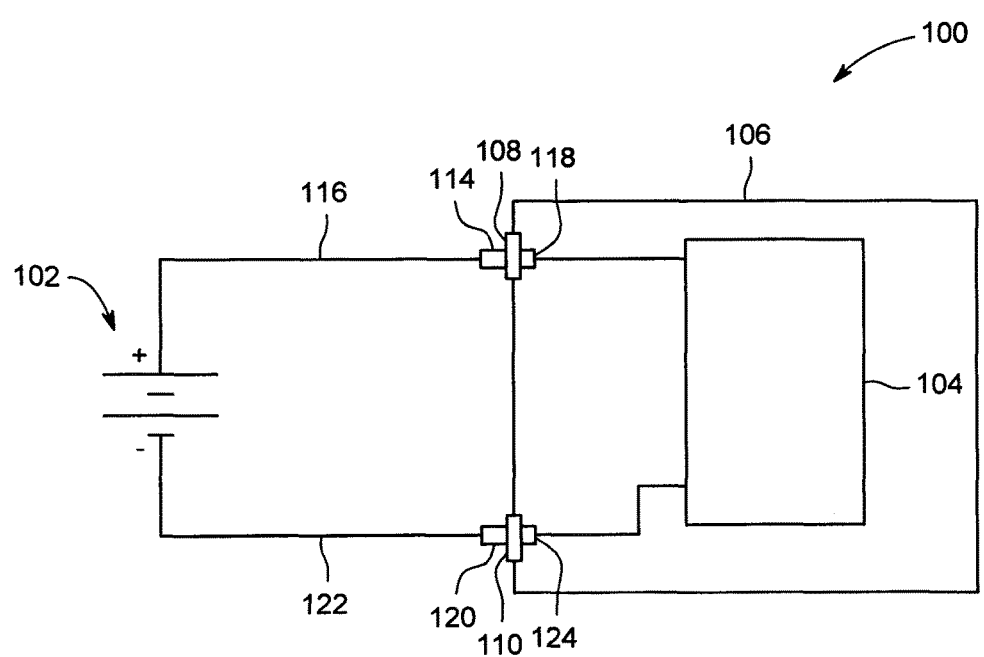
FIG. 1 is a block diagram of an exemplary power conversion system including a feedthrough.

Unless otherwise indicated, the drawings provided herein are meant to illustrate features of embodiments of the disclosure. These features are believed to be applicable in a wide variety of systems comprising one or more embodiments of the disclosure. As such, the drawings are not meant to include all conventional features known by those of ordinary skill in the art to be required for the practice of the embodiments disclosed herein.

DETAILED DESCRIPTION

In the following specification and the claims, reference will be made to a number of terms, which shall be defined to have the following meanings.

The singular forms "a", "an", and "the" include plural references unless the context clearly dictates otherwise.

"Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about" and "substantially", are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

Embodiments of the present disclosure relate to a high current flexible feedthrough. In general, direct current is generated by a power source, such as a photovoltaic ("PV") array, and flows through a power line to the feedthrough. At the feedthrough, the electrical current is passed through a cabinet that houses a fast switching power converter, such as a silicon carbide ("SiC") or gallium nitride power converter. The fast switching power converter converts the direct current to alternating current. In the process, however, high frequency alternating current or noise is generated. The high frequency alternating current flows back into the feedthrough, where it is returned to its source through a plurality of capacitors mounted on a plurality of printed circuit boards of the feedthrough. Thus, the feedthrough significantly reduces the flow of high frequency alternating current onto the power line coupling the feedthrough to the PV array, and, in turn, reduces the ability of this line (and/or the PV array itself) to act as an unwanted antenna transmitter.

The feedthrough further includes one or more flexible conductive elements, which are configured to make a flexible electrical connection between an electrically conductive element that passes through the cabinet and couples the PV array to the power converter. This flexible electrical connection functions to protect the plurality of PCBs from mechanical stress, wear, and damage, as well as to accommodate high current in the thermally expanding and contracting electrically conductive element.

Although generally described herein with respect to a photovoltaic array ("PV array"), the systems described herein are applicable to any type of electric generation system including, for example, solar power generation systems, fuel cells, geothermal generators, hydropower generators, wind generators, all kinds of motors, and/or other devices that generate or consume power from renewable and/or non-renewable energy sources.

Although generally described as a power generation system herein the disclosed technology can be used to power an electrical load in a similar way.

FIG. 1 is a perspective view of an exemplary electrical power generation system 100. Electrical power generation system 100 includes a power source 102, a power converter 104, a cabinet 106, a first feedthrough 108, and a second feedthrough 110.

Power source 102 is a direct current power source, such as a PV array and/or any other suitable direct current electric generation system. Power source 102 thus collects solar energy and converts the collected solar energy to electrical energy. Specifically, power source 102 converts solar energy to direct current.

Power converter 104 converts the direct current to alternating current. More particularly, power converter 104 includes one or more semiconductor switching elements (not shown) and converts direct current, through the switching action of the one or more semiconductor switching elements, to alternating current. Power converter 104 can generate unwanted high frequency alternating current or noise as a byproduct.

Cabinet 106 is a protective enclosure for power converter 104. Cabinet 106 is manufactured from an electrically conductive material, such as a particular metal or an alloy of several metals. Cabinet 106 thus functions as a Faraday Cage for power converter 104.

First feedthrough 108 and second feedthrough 110 are electrical feedthroughs (as described below with reference to FIGS. 2 and 3). First feedthrough 108 is electrically coupled at a first end 114 to power source 102 through a power line 116. First feedthrough 108 is electrically coupled at a second end 118 to power converter 104. Similarly, second feedthrough 110 is electrically coupled at a first end 120 to power source 102 through a power line 122. Second feedthrough 110 is further electrically coupled at a second end 124 to power converter 104. In addition, and as described elsewhere herein, first feedthrough 108 and/or second feedthrough 110 may be flexibly electrically coupled to (or incorporated within) cabinet 106, such that first feedthrough 108 and/or second feedthrough 110 are capable of accommodating mechanical stress resulting from thermal expansion and/or thermal contraction of first feedthrough 108 and/or second feedthrough 110.

Figure 2:
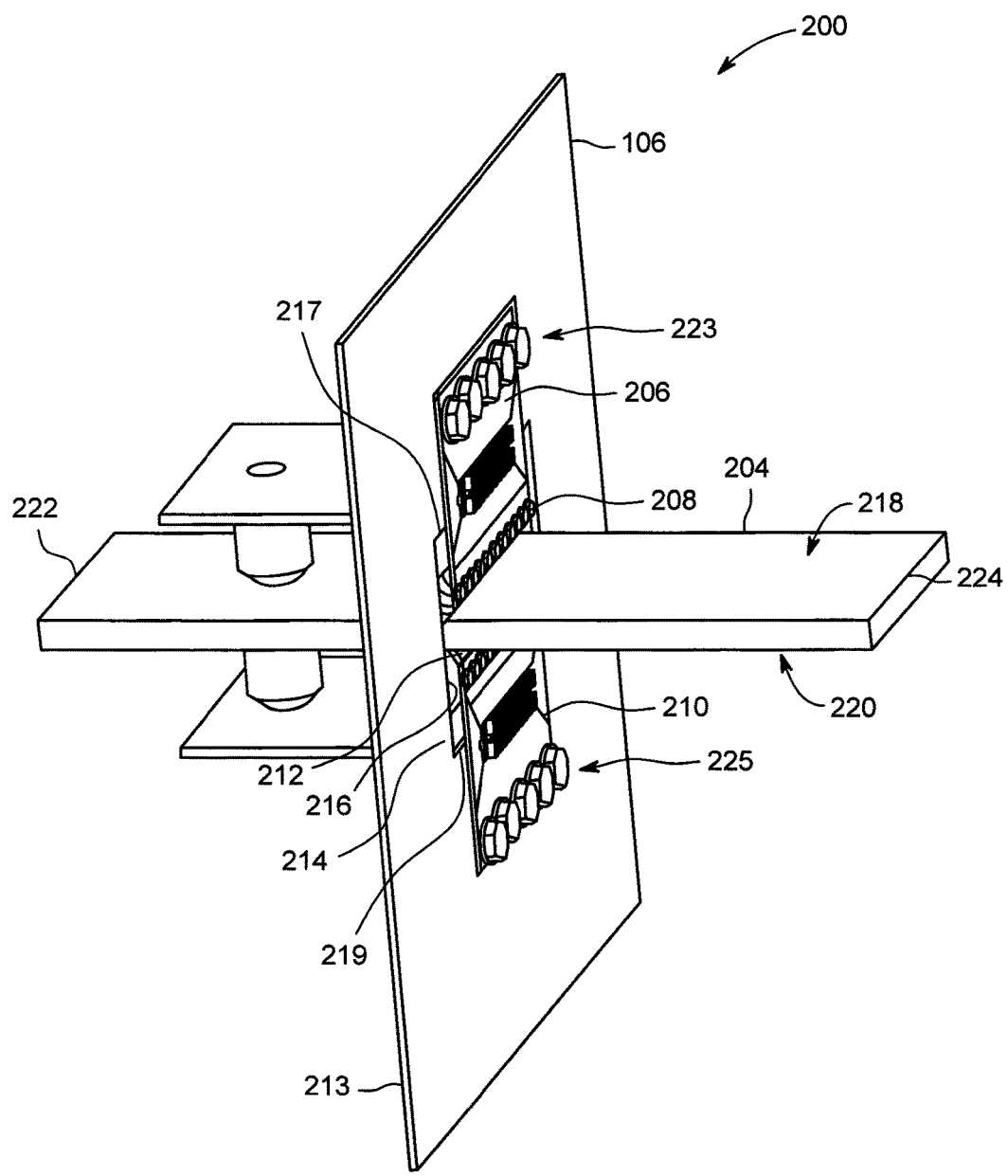
FIG. 2 is a perspective view of the feedthrough shown in FIG. 1.

FIG. 2 is a perspective view of a feedthrough 200, such as feedthrough 108 and feedthrough 110 (shown in FIG. 1). Similarly, FIG. 3 is a side view of feedthrough 200. Feedthrough 200 includes an electrically conductive element 204, a first printed circuit board ("PCB") 206, a first flexible conductive element 208 coupled to first PCB 206, a second PCB 210, and a second flexible conductive element 212 coupled to second PCB 210. First PCB 206 is coupled to cabinet 106 by a first plurality of bolts or other fasteners 223, and second PCB 210 is coupled to cabinet 106 by a second plurality of bolts or other fasteners 225. In the exemplary embodiment, fasteners 223 and 225 are electrically conductive and comprise any suitable conductive material, such as steel, aluminum, brass, copper, tinned copper, or bronze. As used herein, and in various embodiments, first PCB 206 and second PCB 210 may be referred to as first and second electrical assemblies, respectively. Further, in various embodiments, electrical coupling elements other than PCBs may be utilized. For example, in some embodiments, PCBs 206 and 210 may be replaced by ceramic substrates, and the like.

In some embodiments, feedthrough 200 excludes second PCB 210 and second flexible conductive element 212. In other words, in some embodiments, feedthrough 200 includes a single PCB (or another single electrical coupling element, such as a single ceramic substrate), such as first PCB 206 and a single flexible conductive element, such as first flexible conductive element 208. In all other respects, however, an embodiment in which feedthrough 200 includes a single PCB and a single flexible conductive element is identical to or substantially similar to (with the modifications necessary to limit feedthrough 200 to a single PCB and a single flexible conductive element) an embodiment in which feedthrough 200 includes two PCBs 206 and 210 and two flexible conductive elements 208 and 212.

Cabinet 106 includes an outer perimeter 213 and an inner perimeter 214, which defines a passage 216 through cabinet 106. Passage 216 includes a top edge 217 and a bottom edge 219. In the exemplary embodiment, passage 216 is polygonal. In some embodiments, passage 216 is not polygonal, but circular or semi-circular.

Electrically conductive element 204 includes a first surface 218 and a second surface 220 that is diametrically opposed to first surface 218. For example, electrically conductive element 204 is a rigid strip or bar of conductive material (e.g., a "bus bar"), such as copper, tinned copper, brass, or bronze. In some embodiments, electrically conductive element 204 is conductive and cylindrically shaped.

Electrically conductive element 204 extends through passage 216 and is coupled at a first end 222 to a power line, such as power line 116, and at a second end 224 to power converter 104. Thus, electrically conductive element 204 conducts direct electrical current through cabinet 106 to power converter 104.

Figure 3:
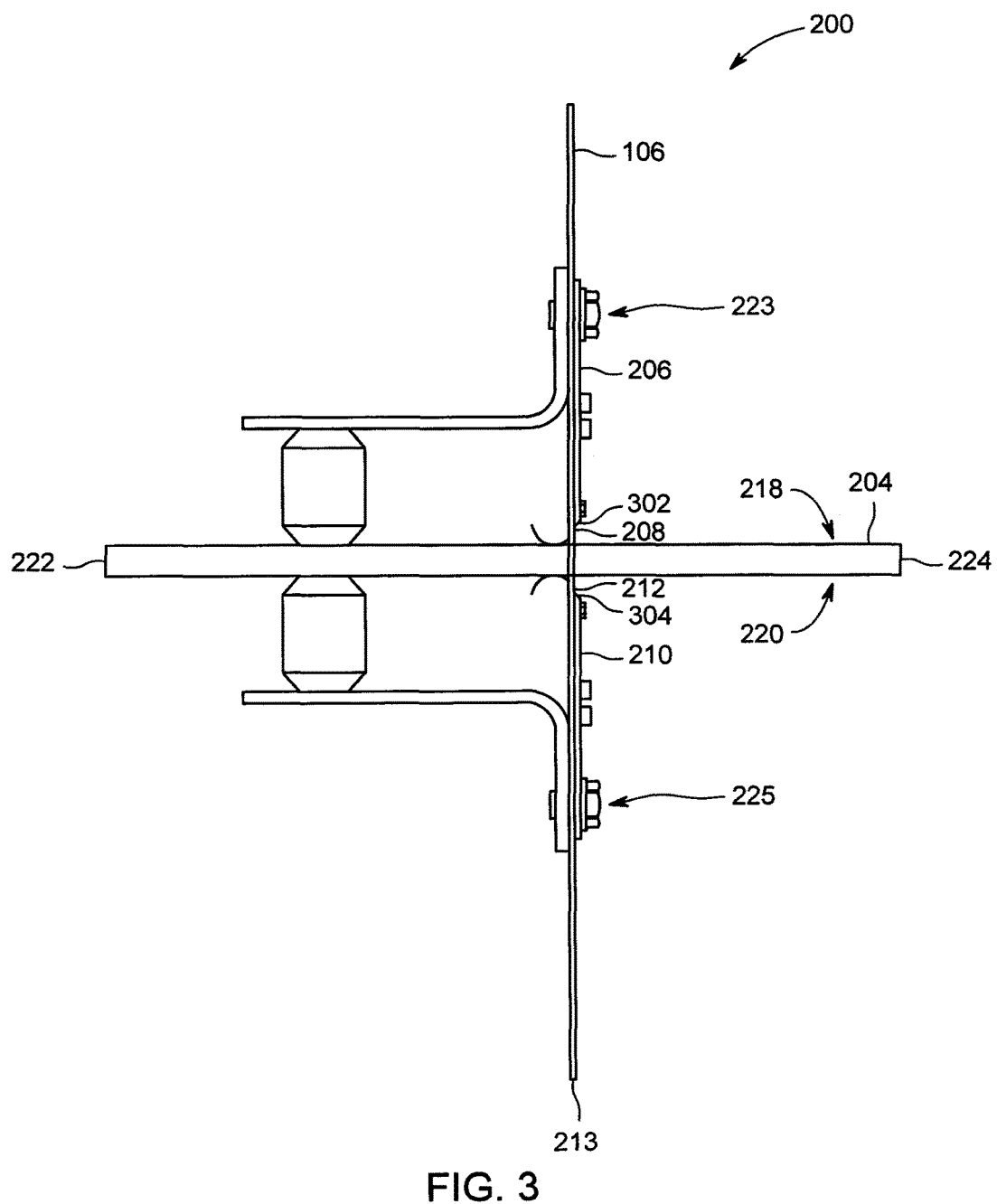
FIG. 3 is a side view of the feedthrough shown in FIG. 1.
Figure 4:
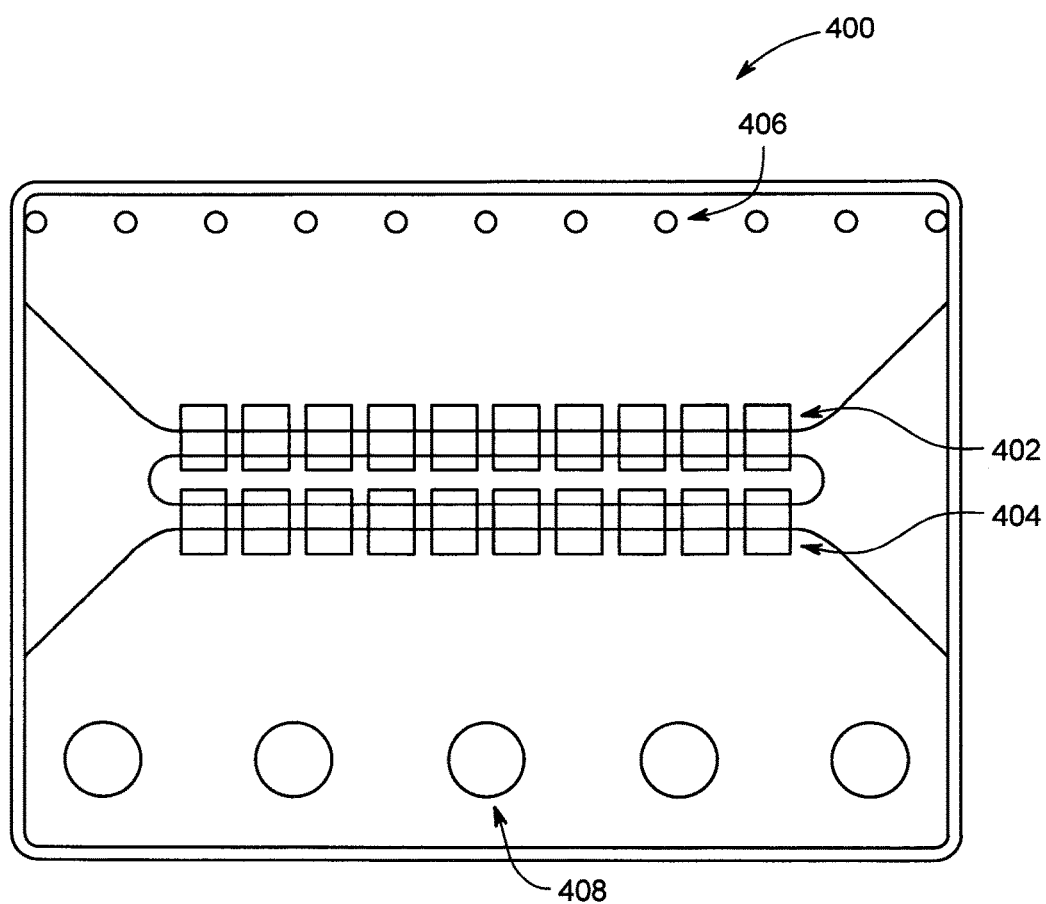
FIG. 4 is a top view of an exemplary printed circuit board of the feedthrough shown in FIG. 1.

FIG. 4 is a top view of an exemplary PCB 400, such as first PCB 206 and second PCB 210, of feedthrough 200 (shown in FIG. 2 and FIG. 3). PCB 400 includes a first plurality of capacitors 402 and a second plurality of capacitors 404. First plurality of capacitors 402 are coupled in parallel. Similarly, second plurality of capacitors 404 are coupled in parallel. First plurality of capacitors 402 are further coupled to second plurality of capacitors 404 in series. Although PCB 400 includes first plurality of capacitors 402 and second plurality of capacitors 404, in some embodiments, PCB 400 only includes a single row of capacitors, such as first plurality of capacitors 402. For example, a number of rows of capacitors may be increased and/or decreased to increase and/or decrease a voltage rating of PCB 400. In addition, in some embodiments, PCB 400 also includes a first plurality of PCB mounting holes 406 and a second plurality of PCB mounting holes 408.

PCB 400 thus functions as a high pass filter to short circuit high frequency current, or a high frequency component of an electrical current, to ground (e.g., through cabinet 106). Specifically, PCB 400 functions as a high impedance circuit for direct electrical current and low frequency alternating current but as a low impedance circuit for high frequency alternating current. Direct electrical current and low frequency alternating current do not therefore flow unimpeded across first plurality of capacitors 402 and second plurality of capacitors 404. However, as described in greater detail below, high frequency alternating current is conducted across first plurality of capacitors 402 and second plurality of capacitors 404 to first plurality of PCB mounting holes 406.

Figure 5:
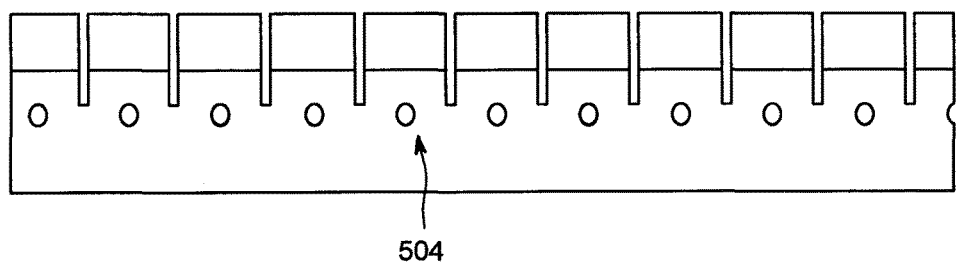
FIG. 5 is a top view of an exemplary flexible conductive element of the feedthrough shown in FIG. 1.

FIG. 5 is a top view of an exemplary flexible conductive element 500, such as first flexible conductive element 208 and second flexible conductive element 212 of feedthrough 200 (shown in FIG. 2 and FIG. 3). In this example, flexible conductive element 500 includes a plurality of mounting holes 504.

Flexible conductive element 500 is an elongated strip of electrically conductive material, such as copper or beryllium-copper. Flexible conductive element 500 is further divided into a plurality of independent and flexible fingers 502. For instance, in some embodiments, flexible conductive element 500 is a finger strip. In the exemplary embodiment, flexible conductive element 500 conducts high frequency alternating current away from electrically conductive element 204.

Figure 7:
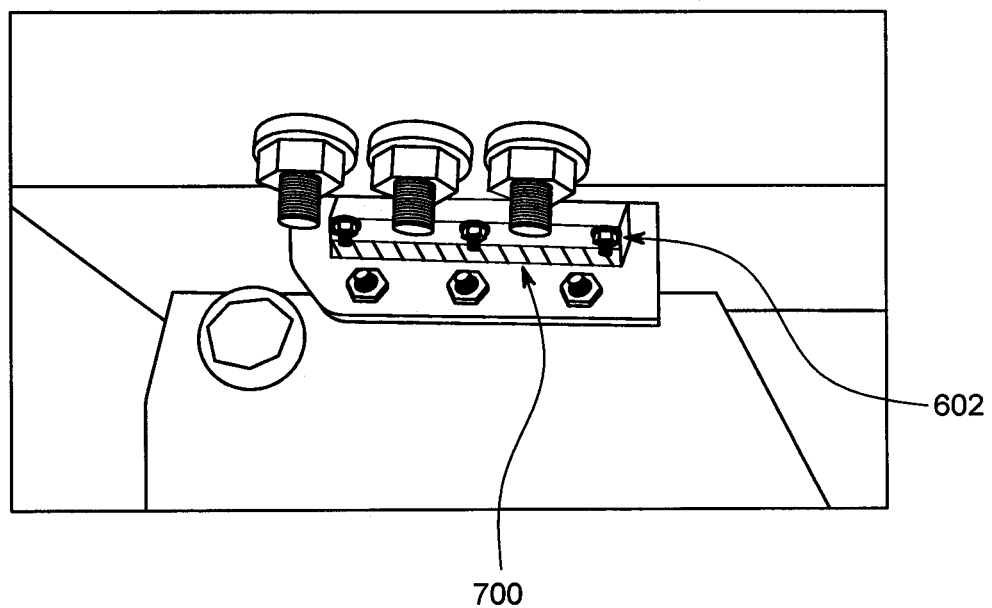
FIG. 7 is a perspective view of an alternative flexible conductive element of the feedthrough shown in FIG. 1.

FIG. 7 is a perspective view of an alternative flexible conductive element 700, such as first flexible conductive element 208 and second flexible conductive element 212 of feedthrough 200 (shown in FIG. 2 and FIG. 3). In this example, flexible conductive element 700 is a high frequency braid, such as a flexible braided or woven electrically conductive material or wire suitable for conducting high frequency alternating current ("HF braid"). In some embodiments, flexible conductive element 700 is copper, tinned copper, or bronze. In the exemplary embodiment, flexible conductive element 700 conducts high frequency alternating current away from electrically conductive element 204.

As described in greater detail below, flexible conductive element 500 and/or flexible conductive element 700 are used to close a gap between PCB 400 and electrically conductive element 204. For example, each finger of the plurality of fingers 502 extends into a gap between PCB 400 and electrically conductive element 204, such that electrically conductive element 204 is placed in flexible electrical contact with PCB 400 through fingers 502.

Figure 6:
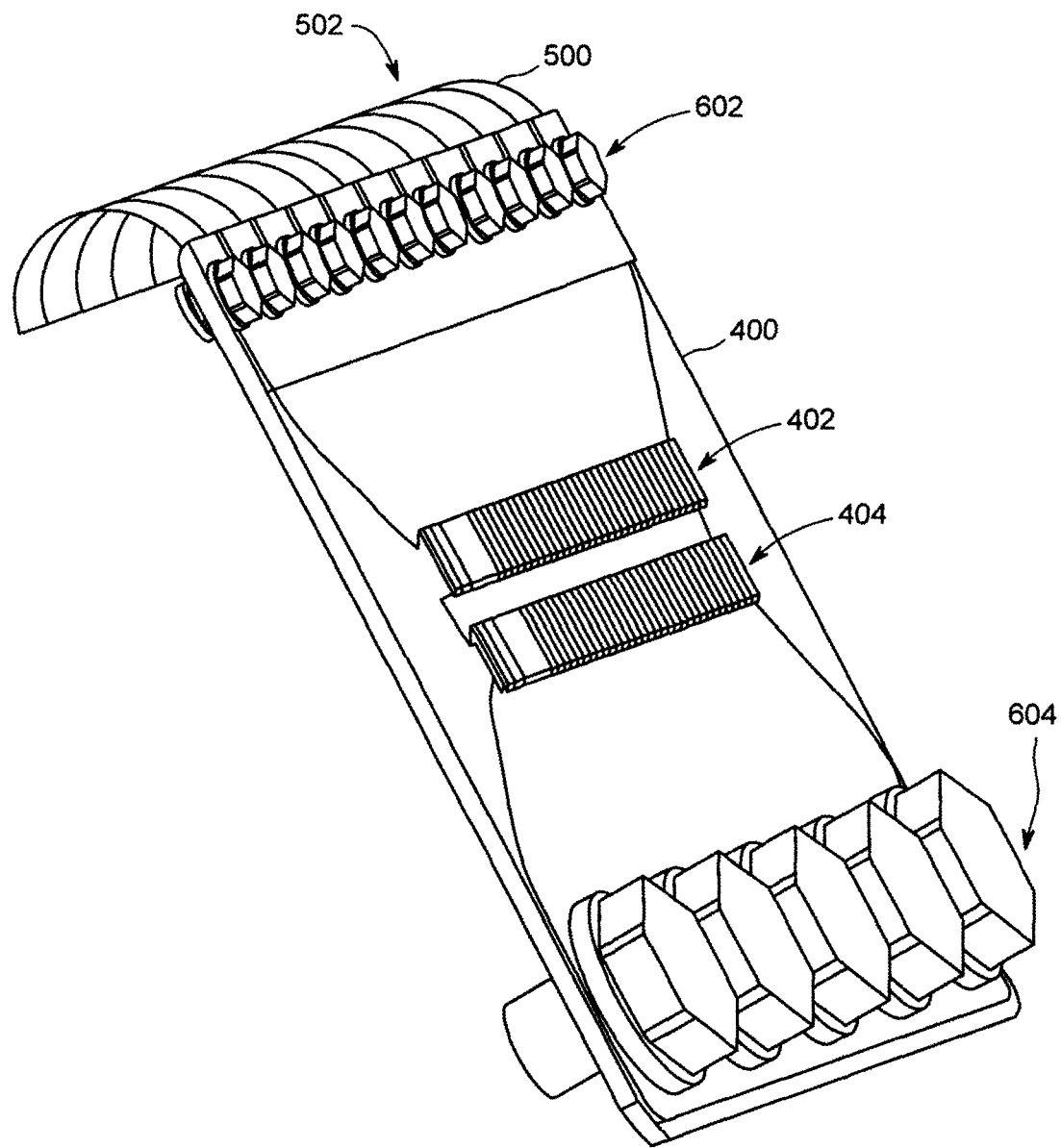
FIG. 6 is a perspective view of the printed circuit board shown in FIG. 4 coupled to the flexible conductive element shown in FIG. 5.

FIG. 6 is a perspective view of PCB 400 coupled to flexible conductive element 500 (shown in FIG. 4 and FIG. 5). A first plurality of bolts or other fasteners 602 extend through each of mounting holes 504 in flexible conductive element 500 and/or through the braid or weave of flexible conductive element 700, as well as through first plurality of PCB mounting holes 406 in PCB 400 to couple flexible conductive element 500 or flexible conductive element 700 to PCB 400. A second plurality of electrically conductive bolts or fasteners 604 extend through second plurality of PCB mounting holes 408 in PCB 400 as well as through cabinet 106 to couple PCB to cabinet 106.

With returning reference to FIG. 2 and FIG. 3, first PCB 206 and second PCB 210 are coupled to cabinet 106, such that a portion of first PCB 206 extends over top edge 217 of passage 216 and a portion of second PCB 210 extends over bottom edge 219 of passage 216. Thus, first PCB 206 extends beyond top edge 217, and second PCB 210 extends beyond bottom edge 219.

In addition, first flexible conductive element 208 is coupled to and extends from an edge 302 or overhangs first PCB 206, such that first flexible conductive element 208 extends further over passage 216. Similarly, second flexible conductive element 212 is coupled to and extends from an edge 304 or overhangs second PCB 210, such that second flexible conductive element 212 extends further over passage 216. First flexible conductive element 208 makes contact with first surface 218 of electrically conductive element 204, and second flexible conductive element 212 makes contact with second surface 220 of electrically conductive element 204.

In operation, electrically conductive element 204 may vary in temperature and, as temperature variations occur, electrically conductive element 204 may expand and contract. In addition, electrical components, such as various fans and/or filter chokes, within system 100 may induce mechanical vibrations in electrically conductive element 204.

To compensate for these thermal variations and mechanical stresses, electrically conductive element 204 is electrically coupled to first PCB 206 through first flexible conductive element 208 and to second PCB 210 through second flexible conductive element 212, such that thermal variations in electrically conductive element 204 and mechanical vibrations traveling through electrically conductive element 204 are not directly transferred to first PCB 206 and second PCB 210. Rather, each flexible conductive element 208 and 212 absorbs or compensates for thermal expansion and mechanical vibrations in system 100 to maintain improved thermal and mechanical isolation between PCBs 206 and 210 and electrically conductive element 204. PCBs 206 and 210 are thus flexibly, rather than rigidly, electrically coupled with electrically conductive element 204 and protected from mechanical stress, damage, and wear, which might otherwise occur as a result of thermal and mechanical alterations in electrically conductive element 204.

In some embodiments, electrically conductive element 204 may be rigidly coupled to first PCB 206 (e.g., through a plurality of bolts or other fasteners). Similarly, in some embodiments, electrically conductive element 204 may be rigidly coupled to second PCB 210 (e.g., through a plurality of bolts or other fasteners). In such an embodiment, a connection between cabinet 106 and first PCB 206 may be flexible (e.g., such as via a finger strip or another flexible connecting element). Likewise, a connection between cabinet 106 and second PCB 210 may be flexible (e.g., such as via a finger strip or another flexible connecting element). Thus, a flexible electrical connection between electrically conductive element 204 and cabinet 106 may be variously achieved and maintained.

First PCB 206 and second PCB 210 are further coupled to cabinet 106, as described above, by a first plurality of fasteners 223 and a second plurality of fasteners 225, respectively. Fasteners 223 and 225 are electrically conductive and function to conduct high frequency alternating current flowing across capacitors 402 and 404, to cabinet 106, and back to power converter 104. Thus, high frequency alternating current flowing on electrically conductive element 204 is prevented from exiting cabinet 106 at passage 216.

Embodiments of the electrical power generation system, as described above, facilitate the transmission of electrical power from a power source, such as a PV array, through a feedthrough, and to a power converter. Embodiments further discourage or limit the introduction of high frequency alternating current on a power line used to transmit electrical power from the power source to the feedthrough. Rather, high frequency alternating current, or noise, is returned to its source through a plurality of capacitors mounted on a PCB of the feedthrough.

Further still, embodiments of the electrical power generation system introduce flexible conductive elements, such as finger strips or high frequency braids, between one or more PCBs and an electrically conductive element to reduce thermal and mechanical wear on the PCBs. Thus, the feedthrough limits the flow of high frequency noise onto the power line connecting the feedthrough to the PV array, and, in turn, radiation of the power line in the RF part of the electromagnetic spectrum as an unwanted antenna transmitter. The feedthrough further protects each PCB from mechanical stress, damage, and wear. The flexible conductive elements of the feedthrough further accommodate a high current, thermally expanding and contracting, electrically conductive element.

Exemplary technical effects of the electrical power generation system described herein include, for example: (a) transmitting low frequency alternating current and direct current from a power source, through a feedthrough coupled to a cabinet, to a power converter; (b) limiting or reducing noise generated by the power converter on the power line connecting the power source to the feedthrough; (c) reducing mechanical stress, damage, and wear on various feedthrough components, such as one or more PCBs of the feedthrough; and (d) accommodating a large current through the feedthrough.

Exemplary embodiments of an electrical power generation system and related components are described above in detail. The system is not limited to the specific embodiments described herein, but rather, components of systems and/or steps of the methods may be utilized independently and separately from other components and/or steps described herein. For example, the configuration of components described herein may also be used in combination with other processes, and is not limited to practice with the systems and related methods as described herein. Rather, the exemplary embodiment can be implemented and utilized in connection with many applications where a feedthrough is desired.

Although specific features of various embodiments of the present disclosure may be shown in some drawings and not in others, this is for convenience only. In accordance with the principles of the present disclosure, any feature of a drawing may be referenced and/or claimed in combination with any feature of any other drawing.

This written description uses examples to disclose the embodiments of the present disclosure, including the best mode, and also to enable any person skilled in the art to practice the disclosure, including making and using any devices or systems and performing any incorporated methods. The patentable scope of the embodiments described herein is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A feedthrough for connecting a direct current (DC) power source to a power converter, the power converter configured to convert direct current received from the DC power source to alternating current (AC), the feedthrough comprising:
    a first printed circuit board configured to function as a first high pass filter to high frequency alternating current generated by the power converter;
    a first flexible conductive element coupled to and extending from an edge of said first printed circuit board;
    a second printed circuit board configured to function as a second high pass filter to high frequency alternating current generated by the power converter; and
    a second flexible conductive element coupled to and extending from an edge of said second printed circuit board.

2. The feedthrough of claim 1, further comprising an electrically conductive element, said electrically conductive element comprising a first surface and a second surface axially opposed to said first surface.

3. The feedthrough of claim 1, wherein said first flexible conductive element comprises a first finger strip and wherein said second flexible conductive element comprises a second finger strip.

4. The feedthrough of claim 1, wherein said first flexible conductive element comprises a first high frequency braid, said first high frequency braid comprising a woven conductive wire, and wherein said second flexible conductive element comprises a second high frequency braid, said second high frequency braid comprising a woven conductive wire.

5. The feedthrough of claim 1, wherein said first printed circuit board is configured to be mounted to a cabinet, and wherein said second printed circuit board is configured to be mounted to the cabinet in axial opposition to said first printed circuit board.

6. The feedthrough of claim 5, wherein said first flexible conductive element and said second conductive flexible element are configured to flexibly close a gap between said first printed circuit board and said second printed circuit board.

7. The feedthrough of claim 1, wherein said first printed circuit board comprises a first plurality of capacitors.

8. The feedthrough of claim 7, wherein said first printed circuit board further comprises a second plurality of capacitors, and wherein said first plurality of capacitors are electrically coupled in parallel, and wherein said second plurality of capacitors are electrically coupled in parallel.

9. An electrical power conversion system for connecting a direct current (DC) power source to a power converter, the power converter configured to convert direct current received from the DC power source to alternating current (AC), the electrical power conversion system comprising:
a cabinet comprising an outer perimeter and an inner perimeter, said inner perimeter defining a passage;
an electrically conductive element, said electrically conductive element comprising a first surface and a second surface axially opposed to said first surface, said electrically conductive element extending through the passage and connecting the power source to the power converter;
a first printed circuit board coupled to said cabinet;
a first flexible conductive element coupled to and extending from an edge of said first printed circuit board to make contact with said first surface of said electrically conductive element, wherein said first flexible conductive element conducts at least a first portion of high frequency alternating current generated by the power converter to said first printed circuit board, and wherein said first printed circuit board conducts the first portion of the high frequency alternating current to ground through said cabinet;
a second printed circuit board coupled to said cabinet; and
a second flexible conductive element coupled to and extending from an edge of said second printed circuit board to make contact with said second surface of said electrically conductive element, wherein said second flexible conductive element conducts at least a second portion of the high frequency alternating current generated by the power converter to said second printed circuit board, and wherein said second printed circuit board conducts the second portion of the high frequency alternating current to ground through said cabinet.

10. The electrical power conversion system of claim 9, wherein said first flexible conductive element comprises a first finger strip and wherein said second flexible conductive element comprises a second finger strip.

11. The electrical power conversion system of claim 9, wherein said first flexible conductive element comprises a first high frequency braid, said first high frequency braid comprising a woven conductive wire, and wherein said second flexible conductive element comprises a second high frequency braid, said second high frequency braid comprising a woven conductive wire.

12. The electrical power conversion system of claim 9, wherein said first printed circuit board is coupled to said cabinet in axial opposition to said second printed circuit board.

13. The electrical power conversion system of claim 12, wherein said first flexible conductive element and said second conductive flexible element are configured to flexibly close a gap between said first printed circuit board and said second printed circuit board.

14. The electrical power conversion system of claim 9, wherein said first printed circuit board comprises a first plurality of capacitors.

15. The feedthrough of claim 14, wherein said first printed circuit board further comprises a second plurality of capacitors, and wherein said first plurality of capacitors are electrically coupled in parallel, and wherein said second plurality of capacitors are electrically coupled in parallel.

16. An electrical power generation system comprising:
a direct current (DC) power source;
a cabinet comprising an outer perimeter and an inner perimeter, said inner perimeter defining a passage;
a power converter mounted within said cabinet, said power converter configured to convert direct current received from the DC power source to alternating current (AC);
an electrically conductive element comprising a first end and a second end, said electrically conductive element further comprising a first surface and a second surface axially opposed to the first surface, said electrically conductive element extending through the passage and coupled to said DC power source at said first end and to said power converter at said second end;
a first printed circuit board coupled to said cabinet;
a first flexible conductive element coupled to and extending from an edge of said first printed circuit board to make contact with said first surface of said electrically conductive element, wherein said first flexible conductive element conducts at least a first portion of high frequency alternating current generated by said power converter to said first printed circuit board and blocks the direct current flowing from said DC power source to said power converter from flowing onto said first printed circuit board;
a second printed circuit board coupled to said cabinet; and
a second flexible conductive element coupled to and extending from an edge of said second printed circuit board to make contact with said second surface of said electrically conductive element, wherein said second flexible conductive element conducts at least a second portion of high frequency alternating current generated by said power converter to said second printed circuit board and blocks the direct current flowing from said DC power source to said power converter from flowing onto said second printed circuit board.

17. The electrical power generation system of claim 16, wherein said first flexible conductive element comprises a first finger strip and wherein said second flexible conductive element comprises a second finger strip.

18. The electrical power generation system of claim 16, wherein said first flexible conductive element comprises a first high frequency braid, said first high frequency braid comprising a woven conductive wire, and wherein said second flexible conductive element comprises a second high frequency braid, said second high frequency braid comprising a woven conductive wire.

19. The electrical power generation system of claim 16, wherein said first printed circuit board is coupled to said cabinet in axial opposition to said first printed circuit board.

20. The electrical power generation system of claim 19, wherein said first flexible conductive element and said second conductive flexible element are configured to flexibly close a gap between said first printed circuit board and said second printed circuit board.

21. A feedthrough for connecting a direct current (DC) power source to a power converter, the power converter configured to convert direct current received from the DC power source to alternating current (AC), the feedthrough comprising:
   a printed circuit board configured to function as a low impedance circuit to at least a portion of high frequency alternating current generated by the power converter, the printed circuit board further configured to function as a high impedance circuit to the direct current flowing from the DC power source to the power converter; and
   a flexible conductive element coupled to and extending from an edge of said printed circuit board.

22. The feedthrough of claim 21, further comprising an electrically conductive element, said electrically conductive element comprising a first surface and a second surface axially opposed to said first surface.

23. The feedthrough of claim 21, wherein said flexible conductive element comprises a finger strip.

24. The feedthrough of claim 21, wherein said flexible conductive element comprises a high frequency braid, said high frequency braid comprising a woven conductive wire.

25. The feedthrough of claim 21, wherein said printed circuit board is configured to be mounted to a cabinet.

26. The feedthrough of claim 25, wherein said flexible conductive element is configured to flexibly close a gap between said printed circuit board and said electrically conductive element.

27. The feedthrough of claim 21, wherein said printed circuit board comprises a first plurality of capacitors and a second plurality of capacitors, said first plurality of capacitors electrically coupled in series with said second plurality of capacitors.

28. The feedthrough of claim 27, wherein said first plurality of capacitors are electrically coupled in parallel and wherein said second plurality of capacitors are electrically coupled in parallel.

29. An electrical power generation system comprising:
   a cabinet;
   a power converter enclosed within said cabinet, said power converter configured to convert direct current received from a DC power source external to said cabinet to alternating current (AC); and
   a feedthrough including:
      at least one electrical assembly;
      at least one flexible conductive element coupled to and extending from an edge of said at least one electrical assembly; and
      an electrically conductive element extending between said cabinet and said power converter, said electrically conductive element in electrical contact with said at least one flexible conductive element, wherein said second electrically conductive element conducts at least a portion of high frequency alternating current generated by said power converter to said electrical assembly and blocks the direct current flowing from the DC power source to said power converter from flowing onto said electrical assembly.

* * * * *